United States Patent
Køhnke (10) Patent No.: US 6,230,712 B1
(45) Date of Patent: May 15, 2001

(54) HEAD IMMOBILIZATION DEVICE

(75) Inventor: Ole Køhnke, Vagetelvej (DK)

(73) Assignee: Ambu International A/S, Glostrup (DK)

( * ) Notice: Subject to any disclaimer, the term of this patent is extended or adjusted under 35 U.S.C. 154(b) by 0 days.

(21) Appl. No.: 09/506,373

(22) Filed: Feb. 18, 2000

Related U.S. Application Data (60) Provisional application No. 60/120,863, filed on Feb. 19, 1999.

(51) Int. Cl.[7] .................................................. A61B 19/00
(52) U.S. Cl. ................................ 128/869; 128/870; 5/637
(58) Field of Search ............................... 128/846, 869, 128/870; 5/630, 637, 638

(56) References Cited

U.S. PATENT DOCUMENTS

| | | | |
|---|---|---|---|
| 4,182,322 | * 1/1980 | Miller | 128/870 |
| 4,297,994 | * 11/1981 | Bashaw | 128/133 |
| 4,928,711 | * 5/1990 | Williams | 128/869 |
| 5,944,016 | * 8/1999 | Ferko | 128/870 |
| 5,988,173 | * 11/1999 | Scruggs | 128/870 |

* cited by examiner

Primary Examiner—Michael A. Brown
(74) Attorney, Agent, or Firm—Levy & Grandinetti (57) ABSTRACT

A head immobilization device, or head immobilizer, is disclosed. The head immobilizer includes an adjustable stable structure obtained by a middle wall standing vertically above the patient's head. The middle wall in an operative condition restricts hinges from up and down movement in a first perpendicular plane, and sideways movement in a second perpendicular plane, while still allowing vertical side walls to be folded flat against the temple areas of a patient's head. This structure permits the head immobilizer to secure a large variety of head sizes. Attachment flanges for the side walls are secured to the board at an angle of approximately 90° to the middle wall. This attachment locks the structure from movement in a third perpendicular plane. The patient's head is prevented from moving forward by a restraining band joining the two side walls across the patient's forehead.

19 Claims, 5 Drawing Sheets

HEAD IMMOBILIZATION DEVICE

I claim the benefit under Title 35, United States Code, § 120 to U.S. Provisional Application Ser. No. 60/120,863, filed Feb. 19, 1999, entitled HEAD IMMOBILIZATION DEVICE.

BACKGROUND OF THE INVENTION

1. Field of the Invention

The present invention relates to head immobilization devices. More specifically, the present invention relates to a head immobilization device for restraining a patient's head during transport on a spine board.

2. Description of Related Art

Head immobilization devices are used by emergency medical technicians to secure an injured patient's head from movement, especially rotational movements of the head.

Numerous devices have been proposed in the past to perform the function of immobilizing or stabilizing the human head and/or neck for emergency purposes. Such devices are extremely important, particularly in emergency situations, in the handling of possible fractures of the cervical spine. In the case of industrial injuries, automobile accidents, and battlefield injuries, it is usually necessary to remove the patient from the injury scene, often under conditions of stress or time pressure, for transport to medical facilities. This removal is almost always accomplished by personnel who are not medical doctors, although they may have had varying amounts of education and training in the handling of injured persons.

In such handling and moving, there is a high risk of aggravation of injuries to the cervical spine if the patient's head and/or neck are not properly immobilized or stabilized.

Many prior art patents disclose devices comprising a rigid board member having straps attached thereto for attachment to a patient to immobilize the head and neck. These devices provide a rigid structure for completely preventing lateral motion and rotation of the patient's head. But they are often expensive, bulky, and complicated to use. They are also frequently impractical to maintain, store, and clean between uses.

Head immobilization devices are usually single use or disposable devices, which do not require sterilization after a use. It is desirable that such disposable immobilizers be sturdy but also inexpensive.

The storage capacity of emergency medical vehicles or ambulances is limited. These vehicles are able to carry more equipment when the equipment can be stowed in a flat or folded condition. Desirable head immobilization devices can be stored in a flat condition and unfolded to an operative condition.

U.S. Pat. No. 4,182,322 discloses a head-restraining and safety support apparatus having a head-rest section at one end. Included is a durable, lightweight, three-section cushion that can be used for safety purposes to cover and restrain effectively the head of an accident victim while being placed on a body splint/litter apparatus in preparation for transport to a medical facility. Two flexible attaching members are connected to the rear edges of the opposing side cushion sections. The attaching members can be fastened to the head section of the body/splint litter apparatus by any convenient fastener such as hooks, snaps, or ties but preferably by the use of Velcro® brand fastening means. A main forehead strap protects and restrains the head from forward motion and a chin strap provides additional restraint and support, both straps being secured by any convenient means at one end of each to the front edge of one side of the cushion member, and fastenable by any convenient means to the outer surface of the opposite cushion section.

U.S. Pat. No. 4,571,757 discloses a device for restraining the head of an injured person carried on a cervical support board, the device having a pair of L-shaped side frames each defining a base portion and a brace portion. The brace portion is sized approximately 6 to 8 inches long (in the direction of the base portion). Hook-loop fasteners, e.g., Velcro®, are fixed to the base portion of the side frames and to the support board where the injured person's head is located. The brace portion of the side frame is adapted then to be snugged against the side of the person's head, extending from close to the neck upward beyond the ears, with the base portion then being secured onto the support in this position. Straps are then trained over the person's head, at the forehead and/or chin, and secured again by hook-loop fasteners to the brace portions of the side frames. Openings in the guide portions of the side frames expose the person's ears for visual and tactual access. Padding on the brace portion surrounds the access opening to cushion the snugging action against the person's head.

U.S. Pat. No. 4,589,407 discloses a spine immobilizer adapted for rendering an accident victim's head and upper body immobile. The spine immobilizer in a preferred form is made of a sheet of corrugated cardboard including a multilayer spine panel to resist longitudinal bending, laterally extending head panels bendable into position adjacent to the sides of the person's head, laterally extending body panels bendable into conformity with the person's upper body, and straps and fastening assemblies for securing the body panels in position. The immobilizer includes box sections providing increased resistance to longitudinal bending, one formed by laterally extending stiffener panels having free ends that can be arranged in overlying relation, and others formed by the strap arrangement. Features include laterally adjustable carrying handles and slot and strap configurations that reduce tearing of the cardboard.

U.S. Pat. No. 4,718,412 discloses a disposable, lightweight, readily stored, low cost cervical spine board made of wax-coated or plastic-coated reinforced double walled corrugated board. The device has precut score lines therein for folding the device around the sides of the head and around the sides of the body. Head and neck tabs and body wings are secured by duct tape or other suitable two-inch tape, which optionally can be preattached to the device.

U.S. Pat. No. 4,928,711 discloses a head immobilizer of the type that can be attached to a rigid backboard support, with the head immobilizer including a base and a pair of laterally extending side support panels. Each of these side support panels further comprises an inner panel and an outer panel, with the inner panel conformable appropriately to the shape necessary for snugly supporting the head to be immobilized. The inner panel also includes an opening that effectively divides a portion of that inner panel into a pair of spaced inner support members extending laterally from the base. The outer panel has inner and outer edges and is hingedly attached adjacent to its inner edge to the inner panel such that it is foldable relative to the inner panel to provide a substantially rigid brace for securing the inner panel in a desired immobilizing position. The outer panel also includes a cutout portion for providing substantial access to the opening of the inner panel when the inner panel is braced in a desired immobilizing position. The outer panel can be secured in a bracing position relative to the inner panel, and the outer panel includes an attachment panel hingedly attached adjacent its outer edge for securing the outer panel in bracing position adjacent the base.

U.S. Pat. No. 4,964,418 discloses a collapsible immobilization device comprising two pieces of treated fiberboard. The pieces are placed one on top of the other and joined together at the center of each. The upper member consists of different sections formed by and attached to each other by fold lines. The fold lines allow these sections to be rotated independent of each other with the fold lines acting as a hinge. When certain sections are folded against a patient's head, they form a cradling area. When the rigid shoulder sections are mated to the base member by means of hook-loop fasteners, e.g., Velcro®, the device becomes rigid, thus restraining the patient's head and neck area. Adhesive tape on the bottom of the base member allows for the device to be secured to a surface that further supports the patient's cervical area.

U.S. Pat. No. 5,211,185 discloses a head immobilization device comprising a foundation portion and a restraining portion. The foundation portion comprises a foundational panel and an adhesive first spine board engaging element situated on the lower surface of the foundation panel. The restraining portion comprises a base panel, two side panels extending laterally from the outer sides of the base panel, and at least one band of material for affixing the side panels to each other in suitable conformance with the patient's head.

U.S. Pat. No. 5,360,393 discloses a dual adhesive strap for securing a patient's head in a head immobilizer. The strap is designed to lie across and adhere to the patient's forehead and have each of its ends adhere to a spine board. The strap has a bottom side comprising a central region which comprises skin contact adhesive flanked by two regions which comprise board contact adhesive. The board contact adhesive is stronger than the skin contact adhesive, such that the strap stays adhered under various environmental conditions and the skin of the patient's forehead is not injured by the skin contact adhesive. The strap and the adhesive regions are preferably large enough to accommodate many sizes of heads, spine boards, and head immobilizers. It is preferred that a removable backing covers the adhesive side of the strap.

SUMMARY OF THE INVENTION

The present invention is directed to a head immobilization device, or "head immobilizer."

More particularly, the present invention is directed to a head immobilizer for use in combination with a spine board, said immobilizer having a substantially rectangular middle wall and substantially rectangular side walls hingedly attached to opposite sides thereof and comprising:

an adjustable stable structure obtained by said middle wall standing vertically above a patient's head, said middle wall in an operative condition restricts hinges from up and down movement in a first perpendicular plane and sideways movement in a second perpendicular plane, said side walls being folded flat against temple areas of said patient's head; and attachment flanges for said side walls for securing to a backboard in an operative condition at an angle of approximately 90° to said middle wall.

The head immobilizer includes an adjustable stable structure obtained by a middle wall standing vertically above the patient's head. The middle wall in an operative condition restricts hinges from up and down movement in a first perpendicular plane and sideways movement in a second perpendicular plane while still allowing vertical side walls to be folded flat against the temple areas of a patient's head. This structure permits the head immobilizer to secure a large variety of head sizes. Attachment flanges for the side walls are secured to the board at an angle of approximately 90° to the middle wall. This attachment locks the structure from movement in a third perpendicular plane. The patient's head is prevented from moving forward by a restraining band joining the two side walls across the patient's head.

In a preferred embodiment, the present invention is directed to a blank for forming a head immobilizer, said blank having an obverse side and a reverse side and comprising:

a middle wall having first and second substantially parallel end edges and first and second substantially parallel side edges;

a first side wall connected to said first side edge of said middle wall by a first line hinge, and a second side wall connected to said second side edge of said middle wall by a second line hinge, each of said first and second side walls having a first side edge joined to said respective side edge of said middle wall, a second side edge parallel to said first side edge, and corresponding first and second opposite parallel end edges; and an attachment flange coupled by line hinges to each of said first end edges of each side wall and said middle wall, each of said attachment flanges having an adhesive element affixed thereto.

In another preferred embodiment, the present invention is directed to a head immobilizer formed from a blank, said head immobilizer comprising:

a middle wall having substantially parallel top and bottom edges and first and second substantially parallel side edges;

a first side wall contiguous with said first side edge of said middle wall and a second side wall contiguous with said second side edge of said middle wall, each of said first and second side walls having a first side edge joined by a first line hinge to a respective side edge of said middle wall, a second side edge parallel to said first side edge, and opposite parallel top and bottom edges;

an attachment flange joined by a second line hinge to each of said bottom edges of each side wall and said middle wall, each attachment flange extending perpendicular to the wall to which it is joined and having affixed thereto means for attaching said head immobilizer to a spine board; wherein each of said side walls is rotatable inward about said first side hinges to form an interior angle ranging from greater than 90° to less than 90° with said middle wall, whereby said side walls can be adjusted to conform to the width of a patient's head at the temples.

It is an object of the present invention to provide a rigid structure for prevention of lateral head motion and rotation of the head by use of a small device, i.e., smaller than the type described, for example, in U.S. Pat. No. 4,964,418, that can easily be stored attached to a spine board without any part of the device extending out over the edges of the board and thereby causing problems during storage and handling.

It is another object of the present invention to provide a head immobilizer wherein the amount of material and manufacturing cost required for its construction are minimized.

It is still another object of the present invention to provide a head immobilizer wherein stabilization is provided by resting against the flat surfaces of the temples just above and in front of the ears of the patient and wherein there is no interference with an extrication collar placed around the patient's neck and jaw.

It is still another object of the present invention to provide a device that can be easily applied to a patient with minimal movement of the patient.

It is still another object of the present invention to provide a device that can be used to secure a patient's head after the patient has been placed upon an apparatus that will be used to support the patient's cervical area.

It is still another object of the present invention to provide a device that is adjustable permitting it to be used for differing head sizes.

It is still another object of the present invention to provide a device that can be secured to a litter, stretcher, table or other substantially flat surface that will assist in the support of the patient's cervical area without that surface or apparatus being specially prepared to accept the device.

It is still another object of the present invention to provide a device that can be supplied and stored in a substantially collapsed or folded condition, whereby only a small storage space is required.

It is still another object of the present invention to provide a device that substantially conforms to the width of a patient's head at the temples, thereby providing greater immobilizing characteristics.

It is still another object of the present invention to provide a device that is inexpensive and can be disposed of after a single use.

It is still another object of the present invention to provide a device that can be made from lightweight materials in order to have enhanced portability.

It is still another object of the present invention to provide a device that can be used in combination with a cervical neck brace.

For a better understanding of the present invention, together with other and further objects thereof, reference is made to the following description taken in connection with the accompanying drawings in which preferred embodiments of the present invention are illustrated, the scope of the invention being pointed out and contained in the appended claims.

DESCRIPTION OF THE PREFERRED EMBODIMENT(S)

The invention is a sturdy head immobilizer that is inexpensive and folds from a substantially flat, inoperative condition, i.e., a blank, into a three-dimensional, boxlike operative condition.

The head immobilizer of the present invention can be made from cardboard; plastics, e.g., sheet plastics, injection molded plastics, or rigid foams; wood; metal; cloth; composite materials; other inexpensive sheet materials; or a combination of any or all to provide a disposable product. Generally, it will be desirable to avoid the use of metal parts so as to allow X-rays to be taken of the patient through the device itself while it is still restraining the person's head. Use of cardboard, especially double-walled, corrugated cardboard, is preferred because it is relatively inexpensive and readily available. If desired, it can be coated with wax, plastic resins, or the like in order to render it waterproof and resistant to absorption and/or staining by blood or other body fluids.

Figure 1:
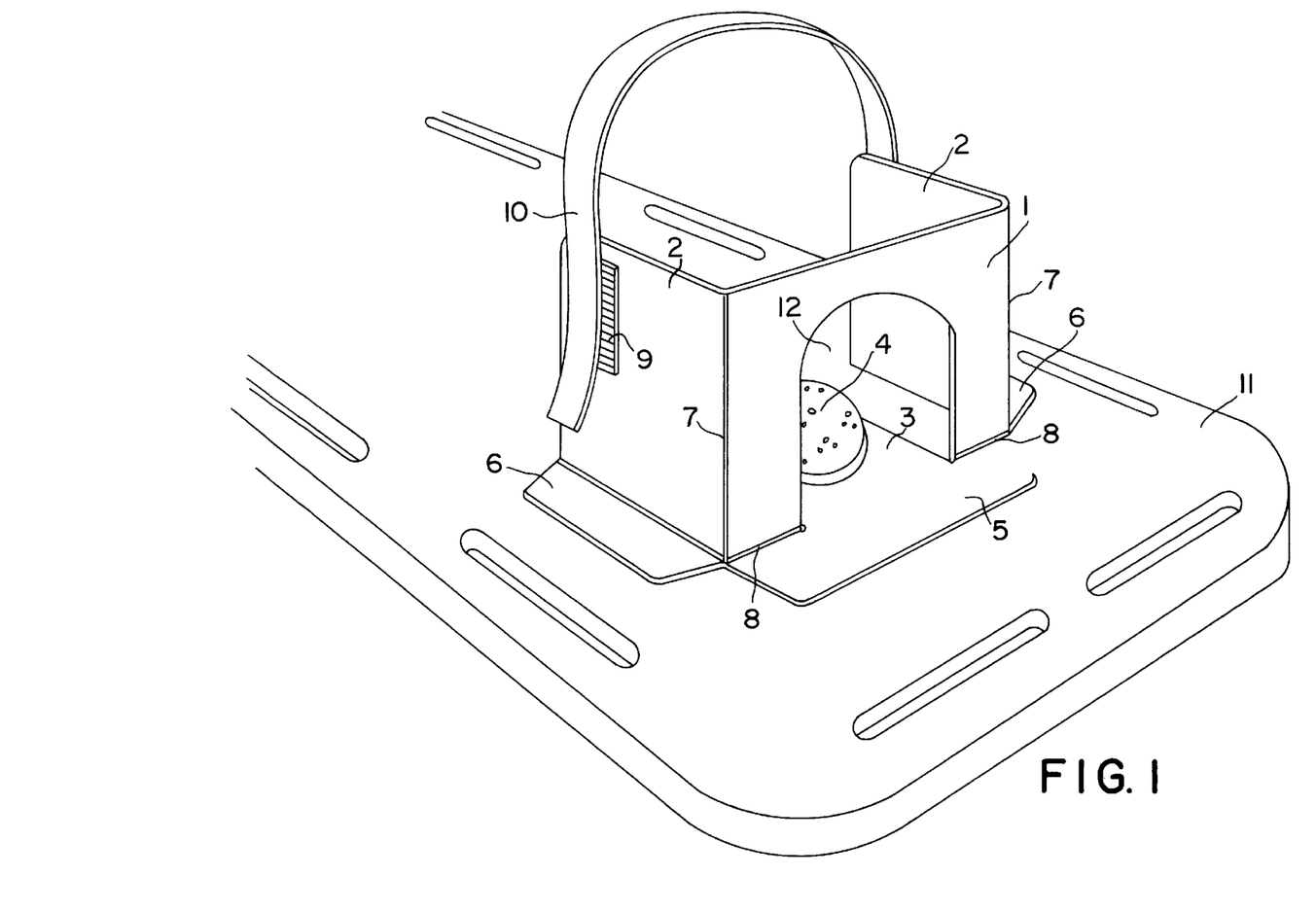
FIG. 1 illustrates a perspective view of a preferred embodiment of the invention attached to a spine board.

FIG. 1 illustrates a perspective view of a preferred embodiment of the head immobilizer in its folded, operative condition attached to a spine board 11. The head immobilizer includes an adjustable stable structure obtained by a middle wall 1 standing vertically with respect to the spine board 11 and above the patient's head (not shown). The middle wall 1 in the operative condition restricts line hinges 7 from up and down movement in a first perpendicular plane and sideways movement in a second perpendicular plane, while still allowing vertical side walls 2 to be folded flat against the temple areas of a patient's head. Attachment flanges 6 for the side walls 2 are secured to the spine board 11 at an angle of approximately 90° to the middle wall 1. This attachment locks the structure from movement in a third perpendicular plane. The patient's head is prevented from moving forward by restraining band 10 joining the two side walls 2 across the patient's forehead.

Figure 2A:
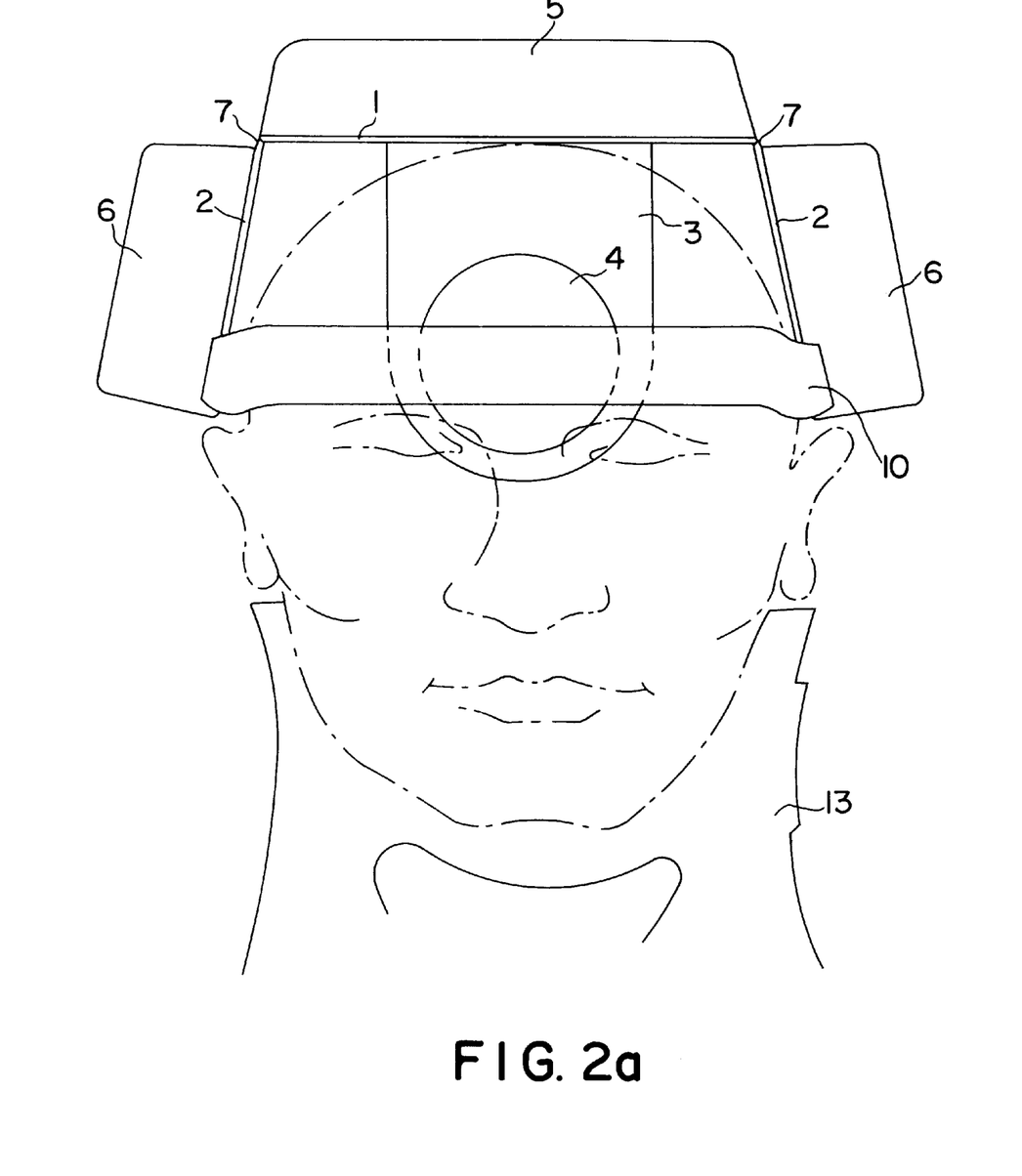
FIGS. 2a and 2b illustrate top views of the device positioned around the head of a large adult and a small child, respectively.
Figure 2B:
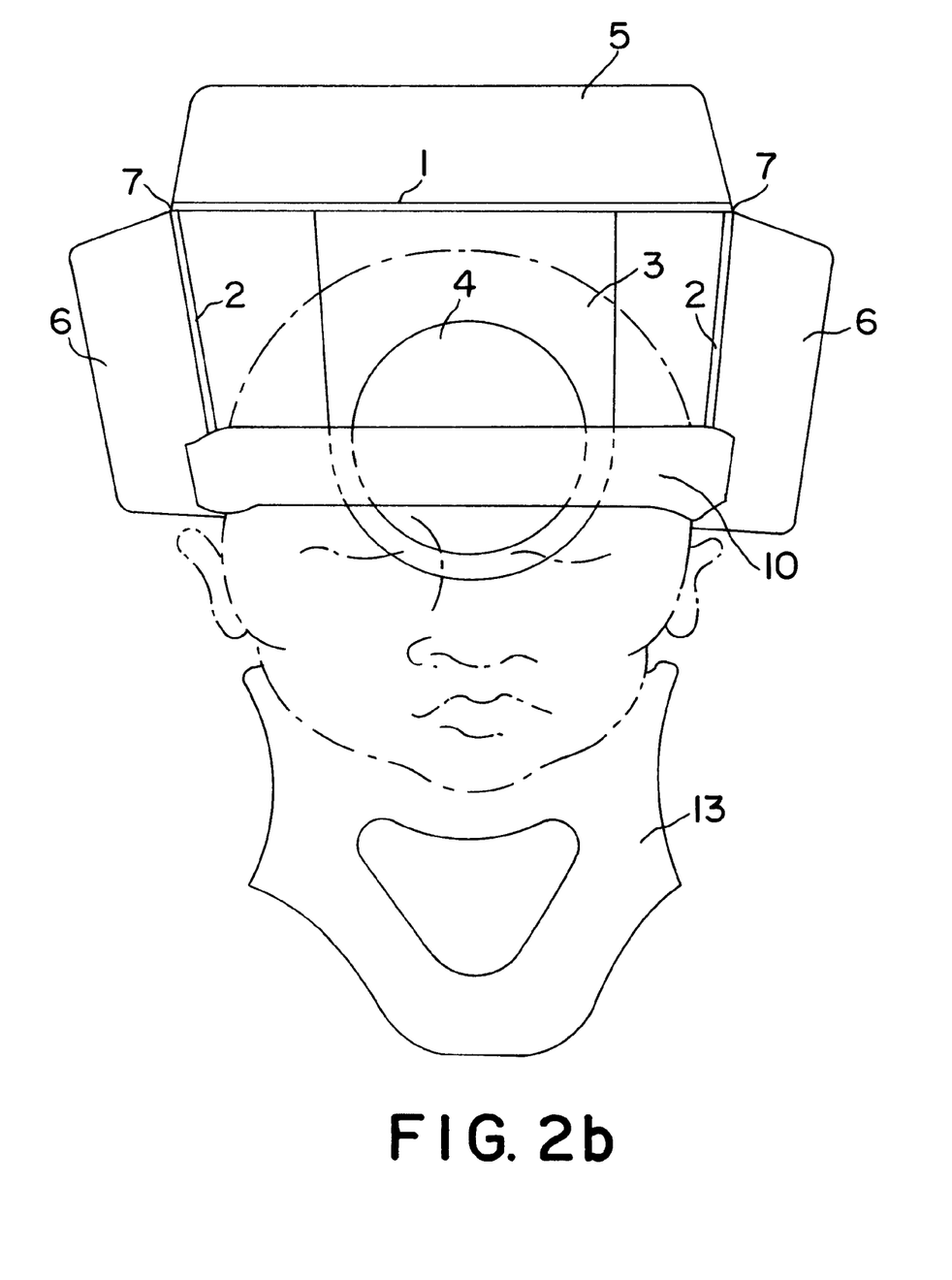

FIGS. 2a and 2b illustrate top views of the device positioned around the head of a large adult and a small child, respectively. The structure of the head immobilizer permits a wide variety of head sizes to be accommodated. The head immobilizer of the present invention in its operative condition provides a stable structure by securing the vertical middle wall 1 and two side walls 2 to the spine board 11. The free corners of the boxlike structure are desirably held together by the restraining band 10 across the patient's forehead. This restraining band 10 prevents both lateral head motion as well as rotation of the head.

Figure 3:
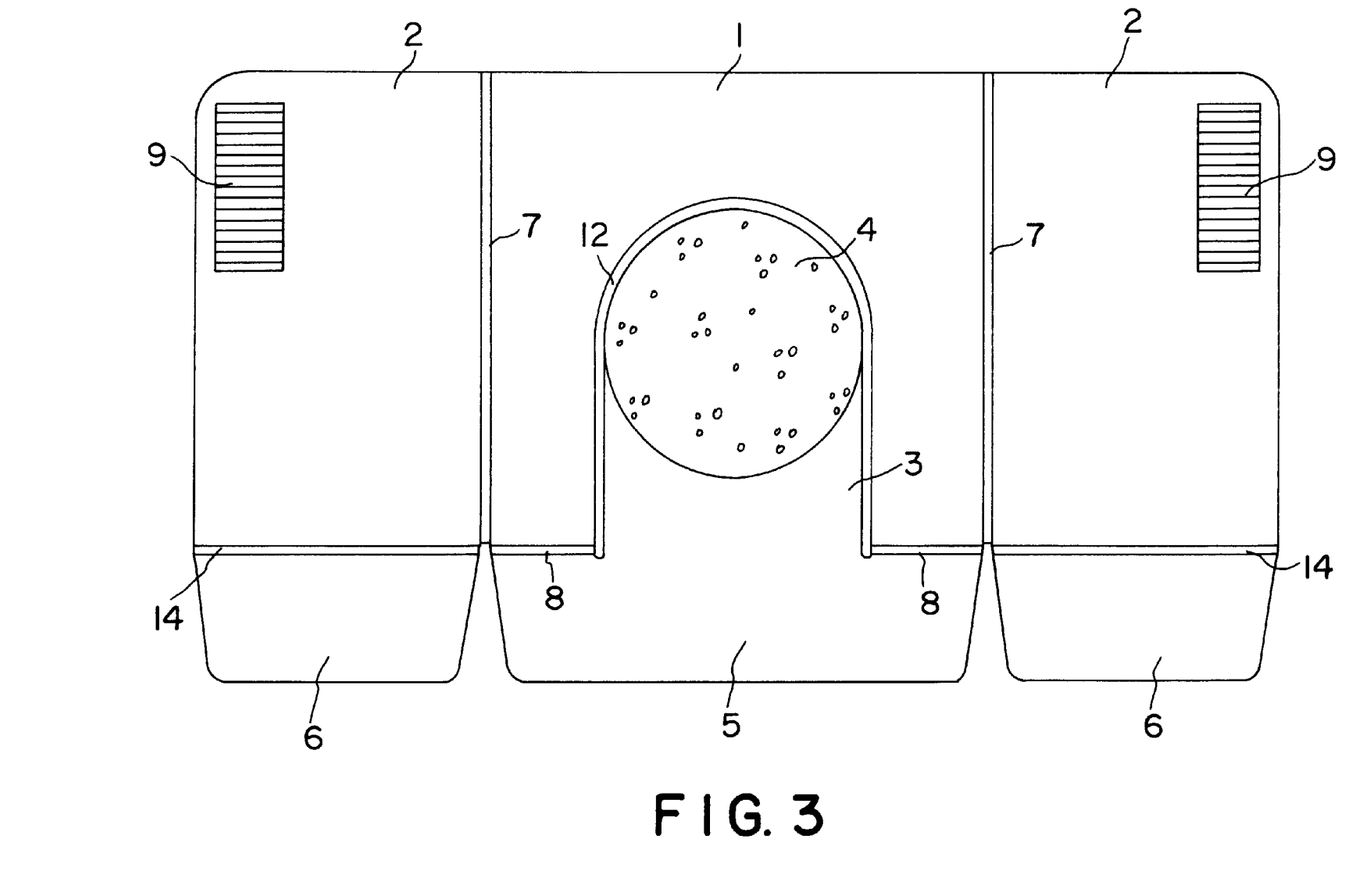
FIG. 3 illustrates a plan view of the obverse surface of an embodiment of the invention in its flat or inoperative condition.
Figure 4:
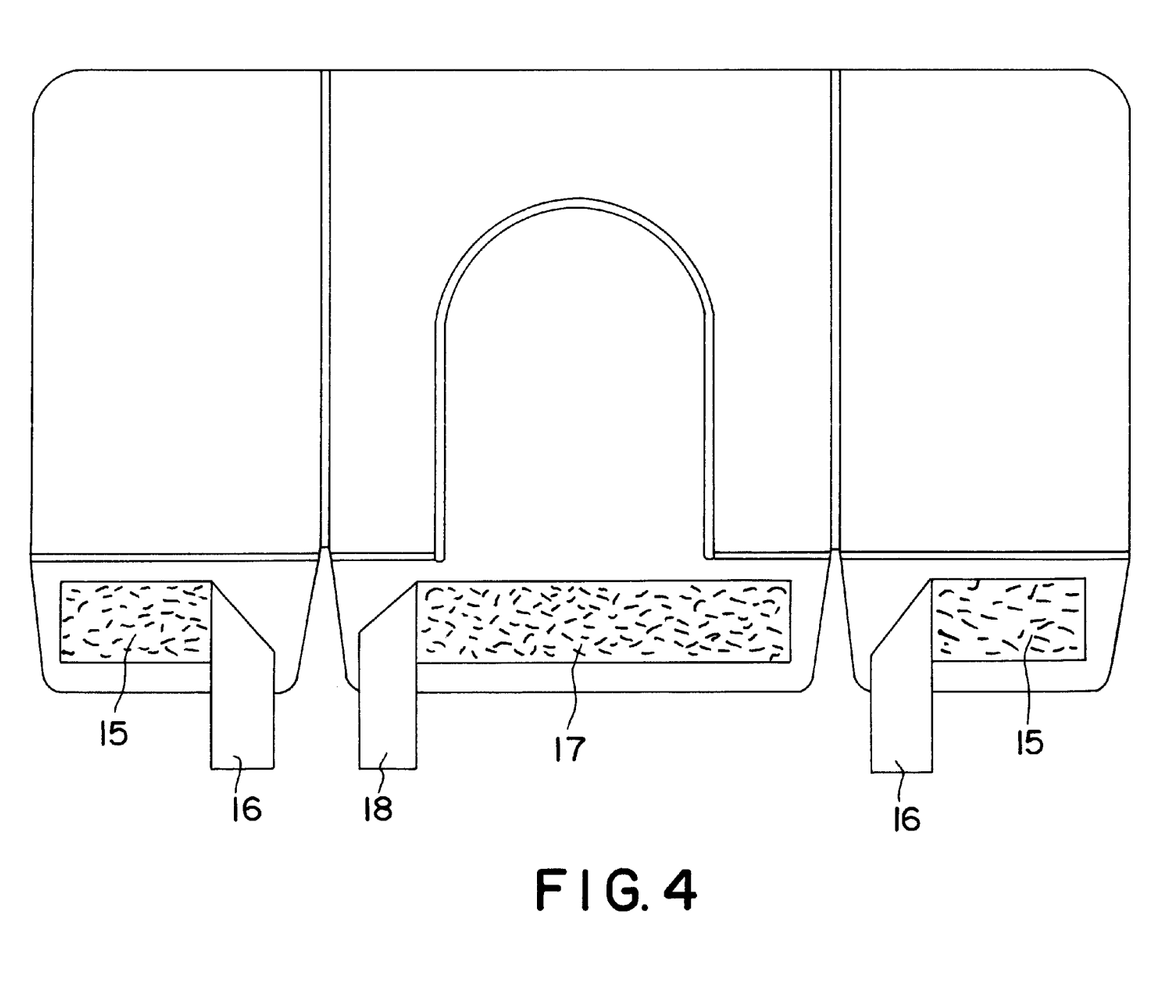
FIG. 4 illustrates a plan view of the reverse surface of the embodiment of FIG. 3 in its flat or inoperative condition.

FIGS. 3 and 4 illustrate, respectively, a plan view of the obverse surface of an embodiment of the invention in its flat, or inoperative, condition and a plan view of the reverse surface of the embodiment in its flat, or inoperative, condition, i.e., the two opposite sides of the blank of the present invention. The walls and flanges of the head immobilizer are flat sheets formed from, for example, corrugated cardboard, sheet plastic, injection molded plastic, or a comparable material. The head immobilizer in the flat condition can be stored in a minimum of space. Alternatively, the head immobilizer, in its flat condition, can be preattached to the spine board 11 at the correct position for folding into the operative condition when needed.

The cutout opening 12 is formed in a substantial U-shape in a preferred embodiment of the invention. Those skilled in the art will understand that there is nothing particularly critical in the shape of the cutout opening 12, which could as well be rectangular or have other archlike configurations. Thus the term "substantial U-shape" is intended to include within its scope these alternative designs. Opening 12 is cut out from the middle wall panel 1 and, when folded downward and inward, forms the head support extension panel 3. Attachment flange 5 forms a T-shaped flat panel structure with the head support extension panel 3 and is attached to the middle wall 1 on both sides of the cutout opening 12 by means of line hinges 8. The line hinges 8 are stamped as score lines in the sheet material or molded as film hinges. The side wall panels 2 are attached to each side edge of the middle wall panel 1 by means of line hinges 7. The line hinges 7 are also stamped as score lines in the sheet material or molded as film hinges. Attachment flanges 6 for the side walls 2 are attached to the lower edges of side walls 2 by means of line hinges 14. The line hinges 14 are stamped as score lines in the sheet material or molded as film hinges.

The width of the middle wall 1 is preferably of a dimension such that the angle between the middle wall 1 and each side wall 2 can range from being greater than 90° when the device is used for immobilizing a large adult head to less than 90° when used on the head of a small child. The width of the side walls 2 must be of a dimension sufficient to allow the edges of side walls 2 to reach the temples just above the ears of a large adult head. It is known to be advantageous for head immobilizers to be configured in such a way that the ears of the patient are at least partially exposed and accessible to medical personnel to aid in providing emergency diagnosis and care. Thus the width of side walls 2 will typically be narrow enough so that they terminate above the ears of the patient. Alternatively, if wider side walls 2 are to be used, it will normally be advantageous to provide notches, openings, or apertures in side walls 2 for location adjacent the patient's ears. In this way exposure of the patient's ear can be provided to permit the patient to hear and to permit an attendant to observe and touch for diagnostic purposes and/or for administering drugs or medication. Specifically, the ear opening can provide important diagnostic information of the extent of injury by the type and amount of any fluid drainage. For example, bleeding from the ears may be indicative of a possible skull fracture.

A foam pad 4 is preferably attached to the head support extension panel 3 on the obverse surface of the device in its flat, or inoperative, condition, as shown in FIG. 3. The foam pad 4 and the head support extension panel 3 to which it is attached will stay flat against the spine board when the middle wall 1 is raised into the operative condition as shown in FIGS. 2a and 2b. Attachment means 9 are fixed to the outer edge of at least one of the side walls 2. In the preferred embodiment shown in FIG. 3, attachment means 9 are fixed to both side walls 2. For example, Velcro® brand or similar hook straps are affixed to the outer surface of at least one side wall 2 to provide suitable attachment means 9 when the restraining band 10 has complementary loop straps attached to its inside surface. It is understood that other conventional strap attachment means 9, such as cam buckles or pressure-sensitive adhesive pads, can be used.

FIG. 4 shows adhesive elements 15 and 17 attached to the reverse surfaces of the attachment flanges 6 and 5, respectively. A suitable and preferred form of adhesive element is double-sided adhesive tape covered by a backing film material. The backing film material desirably extends beyond the adhesive elements 15 and 17 to form extension straps 16 and 18, which can be grasped without lifting the attachment flanges 6 and 5 from the surface of the spine board 11. These extension straps 16 and 18 of the backing film material can be folded back over the full length of the attachment flanges 6 and 5 for removing the backing film with a straight pull. Alternatively, the extension straps 16 and 18 can be folded at 45° angles as shown in FIG. 4 for removing the tape backing by pulling along the edge of the attachment flanges 6 and 5.

The head immobilizer can be folded into its operative condition by pushing on the foam pad 4 through the cutout opening 12. This configuration, as shown in FIG. 3, causes the head support extension panel 3 and the attachment flange 5 to pivot around the line hinges 8 into a 90° angle with the middle wall 1. The attachment flanges 6 are similarly folded outward at the line hinges 14 and the side walls 2 are folded inward in the direction of the foam pad 4. The folded structure is then positioned around the patient's head and the side walls 2 are aligned with the patient's temples just above the ears. When the device is properly aligned, the weight of the patient's head rests on the foam pad 4 and thereby holds the middle wall 1 in position, while the operator presses down on the middle wall 1 and pulls extension strap 18 along the flange 5 to remove the backing material from the adhesive element 17. The attachment flange 5 is pressed firmly against the spine board 11 to secure its bonding to the spine board 11. The side walls 2 are then turned in against the patient's head while pulling the extension straps 16 to expose the adhesive elements 15, and the bonding is secured by pressing firmly on the attachment flanges 6.

In an alternative embodiment of the invention, not shown, attachment flanges 6 are folded inward at the line hinges 14, rather than outward as described above. Those skilled in the art will understand that in this embodiment, adhesive elements 15 and extension straps 16 will be located on the obverse side of attachment flanges 6, rather than the reverse side as shown in FIG. 4.

FIG. 1 illustrates the preferred embodiment of the invention in detail. The vertical middle wall 1 has a cutout opening 12 for access to the head of the patient. The middle wall 1 is attached to the spine board 11 by means of a 90° attachment flange 5 adhesively or otherwise affixed to the spine board 11. Head support extension panel 3 rests against the spine board 11 on the other side of the cutout opening 12 and has a foam pad 4 attached to its upper surface for support of the patient's head. Line hinges 8 are provided between the middle wall 1 and attachment flange 5 on both sides of the cutout opening 12. Side walls 2 are attached to each side of the middle wall 1 by means of line hinges 7, and both side walls 2 are attached to the spine board 11 by means of the 90° attachment flanges 6 adhesively or otherwise affixed to the surface of the spine board 11 following positioning of the side walls 2 against the patient's temples. The restraining band 10 is placed across the patient's forehead and is adjustably attached to the outer portions of both side walls 2.

All the walls and flanges of the structure are made from rigid synthetic material, cardboard, or comparable material. The line hinges are formed by stamping grooves into the sheet material of the walls, gluing, or affixing the walls together with an overlapping film. Alternatively, the walls and flanges can be made by injection molding a film.

The restraining band 10 is adjustably secured to the side walls 2 on at least one side. Securing can be accomplished by affixing means such as Velcro® brand or similar hook and loop tape or other conventional means. An attachment means 9 comprising a strip of Velcro® brand hook material is shown glued to the side wall 2 in this embodiment, and the restraining band 10 has Velcro® brand loop material on its inside surface.

The restraining band 10 can be modified significantly within the scope of the invention. For example, the restraining band 10 can be tape which adheres to the side walls 2 or passes through slots (not shown) in the side walls 2 to form a loop, the end of which can be adhered to itself or the inner surface of the side walls 2. Alternatively, one end of the restraining band 10 can be permanently affixed to one of the two side walls 2. The use of at least one restraining band 10 with the invention is desirable in order to secure a patient's head for transport. The invention can be used to secure a patient's head in emergency situations without the use of a restraining band 10. Also, the use of a plurality of restraining bands 10 (not shown) can also be used.

FIG. 2a shows a top view of an embodiment of the invention as it is used and positioned around the head of a large adult. The side walls 2 are positioned against the patient's temples above the ears as the patient lies on the spine board 11. The side walls 2 desirably form an interior angle greater than 90° with the middle wall 1 and form a stable structure when the attachment flanges 5 and 6 are affixed to the spine board 11. The restraining band 10 is placed across the forehead of the patient and attached to both side walls 2. An extrication collar 13 does not interfere with the side walls 2 of the head immobilizer.

FIG. 2b shows a top view of an embodiment of the invention as it is used and positioned around the head of a small child. The side walls 2 are positioned against the patient's temples above the ears as the patient lies on the spine board 11. This configuration is accomplished by turning the side walls inward to form an interior angle of less than 90° with the middle wall 1 and not placing the patient's head as far inward toward the middle wall 1 as in the embodiment shown in FIG. 2a. The restraining band 10 is pulled across the patient's forehead, and both ends thereof are attached to the attachment means 9 on the side walls 2. An extrication collar 13 does not interfere with the side walls 2 of the head immobilizer.

An alternative embodiment includes preaffixing the head immobilizer to the spine board 11. The operator aligns the device in its flat inoperative condition perpendicular to the center line of the board in a position where the patient's head is to be placed. The adhesive backing is removed from attachment flange 5 of the middle wall 1, and the bonding to the spine board 11 is accomplished by pressing firmly on the attachment flange 5. The spine board 11 may be stored in this embodiment with the head immobilizer attached, ready for use.

This alternative embodiment does not interfere with storage of the spine board 11 or placement of the spine board 11 under a patient. The head immobilizer is brought into the operative condition by grasping the upper edges of the middle wall 1 and both side walls 2 and folding them inward toward the patient's head and at an angle of 90° to the spine board. This configuration causes all three attachment flanges 6 and 5 to fold at the line hinges 8 and 14.

When placing the patient on the board, the operator ensures that the patient's head is in the correct position for use of the head immobilizer before immobilizing the torso on the spine board 11. Head immobilization is then performed by turning the side walls 2 against the patient's temples and securing the attachment flanges 6 to the spine board 11. The restraining band 10 is placed snugly across the patient's forehead and attached to the ends of the side walls 2.

The invention provides an adjustable stable structure through a method of using the head immobilizers. The method involves placing the head immobilizer in the operative position with the middle wall 1 standing vertically with respect to the spine board 11 and above the top of the patient's head, which keeps the line hinges 7 from movement in two perpendicular planes, up-down and sideways. This step still allows the vertical side walls 2 to be turned against the flat temple areas of the patient over a wide variety of head sizes. Once the attachment flanges 6 for the side walls 2 are secured to the spine board 11 at an angle of approximately 90° to the middle wall 1, the structure is locked from movement in the third perpendicular plane. The restraining band 10 across the forehead of the patient to the side walls 2 keeps the patient's head from moving forward.

The preferred embodiment of the invention is a substantially flat structure that obtains its desirable characteristics when folded into the operative condition. However, this folding from a flat condition is not required for proper functioning of the invention. Also, the attachment flanges 5 and 6 for attachment of the head immobilizer to the spine board 11 can be molded to an angle under 90° or can be made from adhesive tape overlapping the lower edges of the vertical walls 1 and 2.

The head support extension panel 3, the foam pad 4, and the cutout opening 12 can also be significantly modified in structure, or even absent from the structure, and the head immobilizer of the present invention can still function.

The benefits of the present invention over the type of head immobilizer described in U.S. Pat. No. 4,964,418, as well as other types known in the art, are numerous. For example, the head immobilizer of the present invention provides a rigid structure for prevention of lateral head motion and rotation of the head. Further, the head immobilizer of the present invention is a small structure that can easily be stored attached to the spine board without any part of the device extending over the edges of the board. Also, much less material is used to manufacture the head immobilizer of the present invention than is typically used in the production of prior art devices, and the design of the present invention permits minimization of manufacturing cost. Additionally, the head immobilizer of the present invention provides stabilization by resting against the flat surfaces of the temples just above the ears of the patient and does not interfere with an extrication collar placed around a patient's neck and jaw.

From the foregoing, it will be obvious to those skilled in the art that various modifications in the above-described device can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated from the appended claims rather than by the foregoing description, and all changes that come within the meaning and range of equivalency of the claims are therefore intended to be embraced therein.

What is claimed is:

1. A blank for forming a head immobilizer, said blank having an obverse side and a reverse side and comprising:
    a middle wall having first and second substantially parallel end edges and first and second substantially parallel side edges;
    a first side wall connected to said first side edge of said middle wall by a first line hinge, and a second side wall connected to said second side edge of said middle wall by a second line hinge, each of said first and second side walls having a first side edge joined to said respective side edge of said middle wall, a second side edge parallel to said first side edge, and corresponding first and second opposite parallel end edges; and
    an attachment flange coupled by line hinges to each of said first end edges of each side wall and said middle wall, each of said attachment flanges having an adhesive element affixed thereto.

2. The blank of claim 1 further comprising a frangible line defining a substantially U-shaped opening in said middle wall.

3. The blank of claim 2 further comprising a foam pad affixed to the obverse side of said middle wall within said defined U-shaped opening.

4. The blank of claim 1 wherein said adhesive elements are affixed to said attachment flanges on the reverse side of said blank.

5. The blank of claim 2 wherein said adhesive elements are affixed to said attachment flanges on the reverse side of said blank.

6. The blank of claim 3 wherein said adhesive elements are affixed to said attachment flanges on the reverse side of said blank.

7. The blank of claim 1 further comprising attachment means affixed to at least one of said side walls on the obverse side of said blank.

8. The blank of claim 2 further comprising attachment means affixed to at least one of said side walls on the obverse side of said blank.

9. The blank of claim 3 further comprising attachment means affixed to at least one of said side walls on the obverse side of said blank.

10. The blank of claim 4 further comprising attachment means affixed to at least one of said side walls on the obverse side of said blank.

11. The blank of claim 5 further comprising attachment means affixed to at least one of said side walls on the obverse side of said blank.

12. The blank of claim 6 further comprising attachment means affixed to at least one of said side walls on the obverse side of said blank.

13. A head immobilizer formed from a blank, said head immobilizer comprising:

a middle wall having substantially parallel top and bottom edges and first and second substantially parallel side edges;

a first side wall contiguous with said first side edge of said middle wall and a second side wall contiguous with said second side edge of said middle wall, each of said first and second side walls having a first side edge joined by a first line hinge to a respective side edge of said middle wall, a second side edge parallel to said first side edge, and opposite parallel top and bottom edges;

an attachment flange joined by a second line hinge to each of said bottom edges of each side wall and said middle wall, each attachment flange extending perpendicular to the wall to which it is joined and having affixed thereto means for attaching said head immobilizer to a spine board; wherein each of said side walls is rotatable inward about said first side hinges to form an interior angle ranging from greater than 90° to less than 90° with said middle wall, whereby said side walls can be adjusted to conform to the width of a patient's head at the temples.

14. The head immobilizer of claim 13 wherein each attachment flange extends outward from the wall to which it is joined.

15. The head immobilizer of claim 14 further comprising a head support extension panel extending inward from said middle wall and in a direction opposite that of the attachment flange joined to said middle wall.

16. The head immobilizer of claim 15 further comprising a foam pad affixed to the upper surface of said head support extension panel.

17. The head immobilizer of claim 13 further comprising a restraining band extending from one side wall to the other side wall and affixed to each side wall by attachment means.

18. The head immobilizer of claim 14 wherein the means for attaching said head immobilizer to a spine board comprises adhesive elements affixed to the underside of said attachment flanges whereby said head immobilizer can be adhered to said spine board.

19. The head immobilizer of claim 18 wherein said adhesive elements are double-sided adhesive tapes covered by a backing film material that extends beyond said adhesive elements to form extension straps.

* * * * *